(12) United States Patent
Tkach et al.

(10) Patent No.: US 11,951,283 B2
(45) Date of Patent: Apr. 9, 2024

(54) HAND-CONTROL DEVICE FOR CONTROLLING OPERATION OF INJECTION SYSTEM

(71) Applicant: ACIST Medical Systems, Inc., Eden Prairie, MN (US)

(72) Inventors: Caleb D. Tkach, Minneapolis, MN (US); Spencer Fodness-Bondhus, Columbia Heights, MN (US); Blaise D. Porter, Minneapolis, MN (US)

(*) Notice: Subject to any disclaimer, the term of this patent is extended or adjusted under 35 U.S.C. 154(b) by 909 days.

(21) Appl. No.: 16/932,123

(22) Filed: Jul. 17, 2020

(65) Prior Publication Data

US 2022/0016341 A1  Jan. 20, 2022

(51) Int. Cl.
*A61B 5/05* (2021.01)
*A61B 6/00* (2006.01)
(Continued)

(52) U.S. Cl.
CPC .......... *A61M 5/16877* (2013.01); *A61B 6/481* (2013.01); *A61M 5/007* (2013.01); *G08B 6/00* (2013.01); *A61M 2005/1403* (2013.01); *A61M 2205/3592* (2013.01); *A61M 2205/502* (2013.01); *A61M 2205/52* (2013.01);
(Continued)

(58) Field of Classification Search
CPC .............. A61M 5/16877; A61M 5/007; A61M 2205/52; A61M 2205/3592; A61M 2205/502; A61M 2205/581; A61M 2205/582; A61M 2205/587; A61B 6/481
See application file for complete search history.

(56) References Cited

U.S. PATENT DOCUMENTS 2,645,224 A   7/1953  Beebe
5,114,664 A   5/1992  Terhune
(Continued)

FOREIGN PATENT DOCUMENTS

EP   1843141 A2   10/2007
EP   2158930 A1    3/2010
(Continued)

OTHER PUBLICATIONS

ACIST CVi® Contrast Delivery System brochure (2016), pp. 1-8.
(Continued)

*Primary Examiner* — Joel F Brutus
(74) *Attorney, Agent, or Firm* — Carlson, Caspers, Vandenburgh & Lindquist, P.A.

(57) ABSTRACT

A hand-control device for controlling the operation of an injection system is described herein. The hand-control device includes one or more input components that receive input to control various operations of the injection system, including commanding the injection to perform a particular operation, changing an operational aspect of the injection system, and selecting an operational mode for the injection system. A communication unit of the hand-control device generates and conveys a signal for the injection system, and receives a command signal from the injection system. An output component outputs an indication, such as a light emission, a sound, or haptic feedback, in response to receiving the command signal. In some instances, this indication acts as a confirmation or failure of the intended input.

38 Claims, 10 Drawing Sheets

(51) Int. Cl.
*A61M 5/00* (2006.01)
*A61M 5/168* (2006.01)
*G08B 6/00* (2006.01)
*A61M 5/14* (2006.01)

(52) U.S. Cl.
CPC . *A61M 2205/581* (2013.01); *A61M 2205/582* (2013.01); *A61M 2205/587* (2013.01)

(56) References Cited

U.S. PATENT DOCUMENTS

| | | |
|---|---|---|
| 5,336,053 A | 8/1994 | Wynkoop |
| 5,515,851 A | 5/1996 | Goldstein |
| 5,916,165 A | 6/1999 | Duchon et al. |
| 6,485,471 B1 | 11/2002 | Zivitz et al. |
| 6,935,163 B2 | 8/2005 | Stewart et al. |
| 8,118,780 B2 | 2/2012 | Fago et al. |
| 2003/0181851 A1 | 9/2003 | Mann et al. |
| 2003/0225380 A1 | 12/2003 | Redl et al. |
| 2006/0129084 A1 | 6/2006 | Miyato |
| 2009/0088732 A1 | 4/2009 | Villegas |
| 2009/0221914 A1* | 9/2009 | Barrett .............. A61M 5/14216 600/431 |
| 2010/0160860 A1 | 6/2010 | Celantano et al. |
| 2010/0262078 A1 | 10/2010 | Blomquist |
| 2010/0331779 A1 | 12/2010 | Nystrom et al. |
| 2014/0142535 A1 | 5/2014 | Imhof et al. |
| 2015/0209515 A1* | 7/2015 | Houde .................... A61M 5/19 600/432 |
| 2018/0360688 A1* | 12/2018 | Lee ................... A61M 5/16877 |

FOREIGN PATENT DOCUMENTS

| | | |
|---|---|---|
| JP | 11351999 A | 12/1999 |
| WO | 9924094 A1 | 5/1999 |

OTHER PUBLICATIONS

PCT Partial International Search Report dated Nov. 4, 2021 for related International Application No. PCT/US2021/041915, 10 pages.

* cited by examiner

HAND-CONTROL DEVICE FOR CONTROLLING OPERATION OF INJECTION SYSTEM

TECHNICAL FIELD

The disclosure relates to fluid injection systems.

BACKGROUND

Many medical imaging procedures, such as angiography, involve injecting a contrast fluid into a patient. Angiography is a procedure used in the diagnosis and treatment of cardiovascular conditions, including abnormalities or restrictions in blood vessels. During angiography, a radiographic image of the heart or vascular structure is obtained by injecting contrast fluid through a catheter into the vasculature (e.g., the coronary artery) of the patient. The injected contrast fluid can pass to vascular structures in fluid communication with the blood vessel in which the injection is made. X-rays are passed through the region of the body in which the contrast fluid was injected. The X-rays are absorbed by the contrast fluid, causing a radiographic outline or image of the vasculature containing the contrast fluid. Contrast injection can be used in conjunction with other medical procedures as well, such as optical coherence tomography (OCT) imaging, intravascular ultrasound (IVUS) imaging, computed tomography (CT) imaging, magnetic resonance imaging (MRI), and interventional device procedures/placements.

SUMMARY

In general, the disclosure describes a hand-control device configured to control various operational aspects of an injection system. In some examples, previous hand-control devices may be limited to two buttons, thereby limiting the functionality. To be consistent with previous designs, the hand-control device described herein may also include two buttons, but may incorporate additional technology to provide the hand-control device with additional functionality.

For instance, to facilitate two-way communication between the hand-control device and the injection system, the hand-control device may be further configured to, after conveying an injection system command signal to the injection system, receive a controller command signal from the injection that is indicative of the alteration performed on an operational aspect of the injection system. This indication can be visual (e.g., lights), haptic (e.g., vibrations), or audible (e.g., sounds).

In another instance, rather than performing specific functions to the two buttons, hand-control device may instead assign a mode selection operation to a first input component and an action to a second input component. As such, the operator may toggle between any number of modes using the mode selection input component before commanding the injection system to perform the action associated with the selected mode.

In still another instance, rather than being forced to press an action button twice to cease a refilling action and begin a delivery action, a hand-control device may detect when the user picks up the hand-control device, through motion detection modules and/or touch modules (e.g., when the user touches a button or touches the hand-control device itself). Upon detecting this motion or contact, the hand-control device may issue a command to cease the refill operation. Conversely, when the hand-control device has not moved or been contacted for a threshold amount of time, the hand-control device may issue a command to resume or begin a refill operation.

Implementing the hand-control device into an injection system as described herein provides multiple benefits. For instance, rather than force the user to use a separate touchscreen to perform additional control functions, the hand-control device described herein may control additional functions without increasing the amount of input components present on the hand-control device. Additionally, by providing feedback at the hand-control device, a user of the hand-control device may maintain their focus on the patient and the activity being performed rather than divert their attention to a different system that the user must analyze to determine if the proper action was completed. Further, by automatically ceasing the refill operation in response to detecting movement of the hand-control device, a user may decrease the amount of explicit inputs that must be entered on the hand-control device, thereby increasing the efficiency of the refill operation, as well as the durability of the hand-control device itself. In the same vein, by automatically resuming the refill operation, or automatically beginning a refill operation, in response to detecting a lack of movement or contact, the various fluid reservoirs used by the injection system may refill at the most efficient and effective times, ensuring that the fluid is available when needed by the operator of the injection system.

Additionally, and importantly, the operator of the hand-control device must be sterile. However, the injection system touchscreen is not sterile. As such, the operator, such as a cardiologist, must either instruct another individual, who may not be a trained cardiologist, as to what actions must be performed by the injection system through the touchscreen, or the cardiologist must themselves perform the functions on the touchscreen through a sterile drape, which can be cumbersome. By adding functionality to the hand-control device, the amount of functionality that the operator may control personally and without having to interact with a drape is greatly increased, thereby increasing the efficiency and efficacy of the overall injection system.

In one example, the disclosure is directed to a method for controlling an injection system using a hand-control device. The method includes receiving, by the hand-control device, user input at an input component of the hand-control device. The method also includes, responsive to receiving the user input: generating, by the hand-control device, an injection system command signal, conveying, by the hand-control device, the injection system command signal to the injection system, and receiving, by the hand-control device, a controller command signal from the injection system. The method further includes outputting, by the hand control device, an indication in response to receiving the controller command signal from the injection system.

In another example, the disclosure is directed to a hand-control device for an injection system. The hand-control device includes a controller body sized to be held in a single hand of a user. The hand-control device also includes an input component at the controller body, wherein the input component is configured to receive user input. The hand-control device further includes a communication unit configured to, responsive to the input component receiving the user input: generate an injection system command signal, convey the injection system command signal to the injection system, and receive a controller command signal from the injection system. The hand-control device also includes an output component at the controller body, wherein the output component is configured to output an indication in response to the communication unit receiving the controller command signal from the injection system.

In another example, the disclosure is directed to a computer-readable medium containing instructions for controlling an injection system using a hand-control device. The instructions cause one or more processors to receive user input from an input component of the hand-control device. The instructions further cause the one or more processors to, responsive to receiving the user input: generate an injection system command signal, convey the injection system command signal to the injection system, and receive a controller command signal from the injection system. The instructions also cause the one or more processors to further output an indication in response to receiving the controller command signal from the injection system.

In another example, the disclosure is directed to a method for controlling an injection system using a hand-control device. The method includes receiving, by the hand-control device, user input identifying an injection system operational mode, the input being received at a first input component of the hand-control device. The method also includes, responsive to receiving the user input at the first input component: generating, by the hand-control device, an injection mode selection signal corresponding to the identified injection system operational mode, and conveying, by the hand-control device, the injection mode selection signal to the injection system. The method further includes receiving, by the hand-control device, user input identifying an action command, the user input being received at a second input component of the hand-control device. The method also includes, responsive to receiving the user input at the second input component: generating, by the hand-control device, an injection command signal corresponding to the identified action command, and conveying, by the hand-control device, the injection command signal to the injection system.

In another example, the disclosure is directed to a hand-control device for an injection system. The hand-control device includes a controller body sized to be held in a single hand of a user. The hand-control device also includes a first input component at the controller body, wherein the first input component is configured to receive user input identifying an injection system operational mode. The hand-control device further includes a communication unit configured to, responsive to the first input component receiving the user input: generate an injection mode selection signal corresponding to the identified injection system operational mode, and convey the injection mode selection signal to the injection system. The hand-control device also includes a second input component at the controller body, wherein the second input component is configured to receive user input identifying an action command for the identified injection system operational mode. The communication unit is further configured to, responsive to the second input component receiving the user input: generate an injection command signal corresponding to the identified action command, and convey the injection command signal to the injection system.

In another example, the disclosure is directed to a computer-readable medium containing instructions for controlling an injection system using a hand-control device. The instructions cause one or more processors to receive user input identifying an injection system operational mode, the input being received from a first input component of the hand-control device. The instructions further cause the one or more processors to, responsive to receiving the user input at the first input component: generate an injection mode selection signal corresponding to the identified injection system operational mode, and convey the injection mode selection signal to the injection system. The instructions also cause the one or more processors to further receive user input identifying an action command, the user input being received from a second input component of the hand-control device. The instructions further cause the one or more processors to, responsive to receiving the user input at the second input component: generate an injection command signal corresponding to the identified action command, and convey the injection command signal to the injection system.

In another example, the disclosure is directed to a method for controlling an injection system using a hand-control device. The method includes receiving, by the hand-control device, user input at an input component of the hand-control device. The method also includes, responsive to receiving the user input: generating, by the hand-control device, a first injection system command signal, and conveying, by the hand-control device, the first injection system command signal to the injection system. The method further includes detecting, by the hand-control device, movement of a controller body of the hand-control device. The method also includes, responsive to detecting the movement of the controller body: generating, by the hand-control device, a second injection system command signal, and conveying, by the hand-control device, the second injection system command signal to the injection system.

In another example, the disclosure is directed to a hand-control device for an injection system. The hand-control device includes a controller body sized to be held in a single hand of a user. The hand-control device also includes an input component at the controller body, wherein the input component is configured to receive user input. The hand-control device further includes a communication unit configured to, responsive to the input component receiving the user input: generate a first injection system command signal, and convey the first injection system command signal to the injection system. The hand-control device also includes a movement detection component at the controller body, wherein the movement detection component is configured to detect movement of the controller body. The communication unit is further configured to, responsive to the movement detection detecting movement of the controller body: generate a second injection system command signal, and convey the second injection system command signal to the injection system.

In another example, the disclosure is directed to a computer-readable medium containing instructions for controlling an injection system using a hand-control device. The instructions cause one or more processors to receive user input from an input component of the hand-control device. The instructions further cause the one or more processors to, responsive to receiving the user input: generate a first injection system command signal, and convey the first injection system command signal to the injection system. The instructions also cause the one or more processors to detect movement of a controller body of the hand-control device. The instructions further cause the one or more processors to, responsive to detecting the movement of the controller body: generate a second injection system command signal, and convey the second injection system command signal to the injection system.

The details of one or more examples of the disclosure are set forth in the accompanying drawings and the description below. Other features, objects, and advantages of the disclosure will be apparent from the description and drawings, and from the claims.

DETAILED DESCRIPTION

Figure 1:
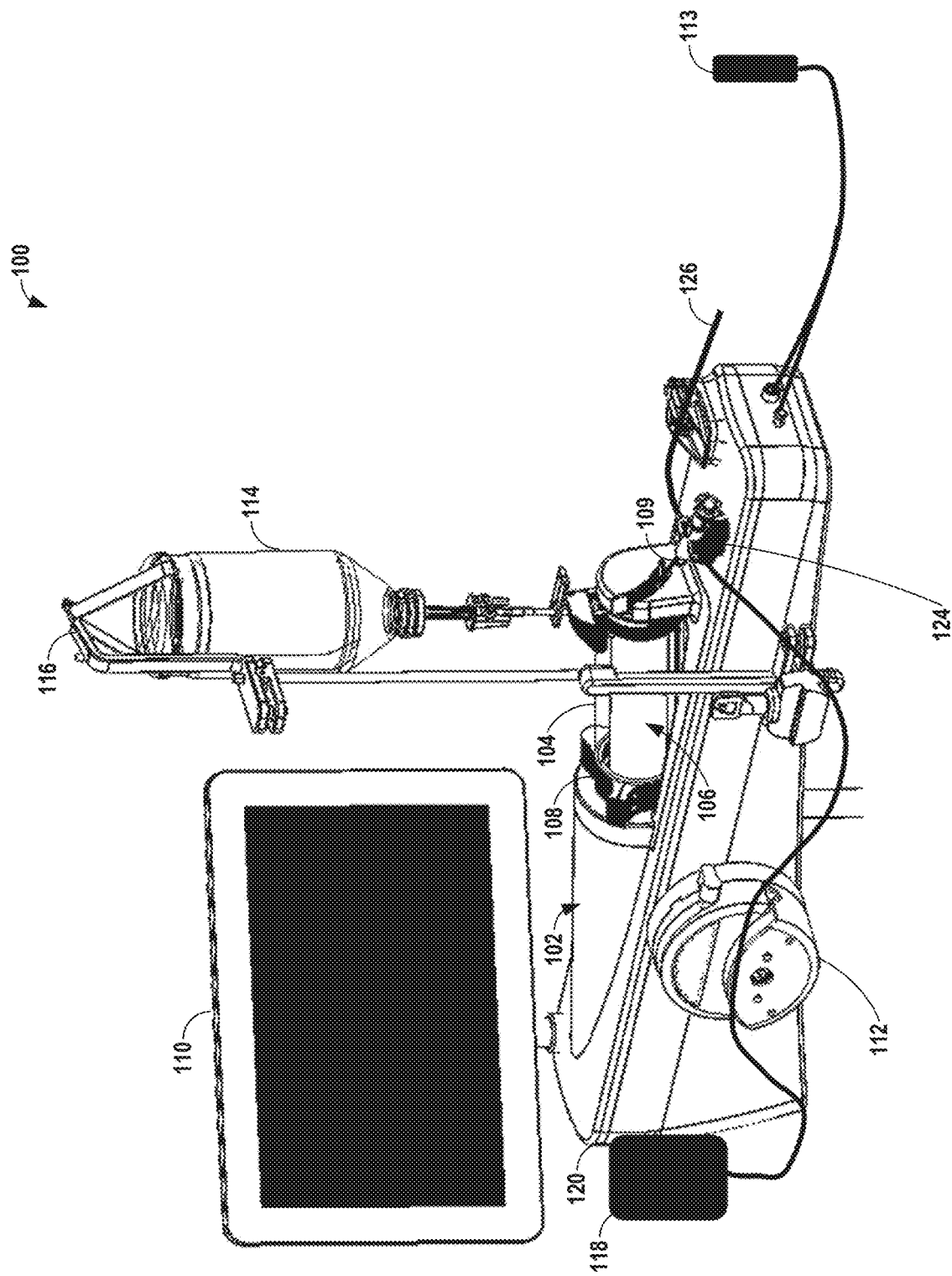
FIG. 1 illustrates a perspective view of an example of a powered fluid injector, in accordance with one or more aspects of the techniques described in this disclosure.

FIG. 1 is a perspective view of an example of a powered fluid injector 100. In operation, the powered fluid injector 100 can inject a quantity of fluid into a patient, for instance into a vessel of a patient via a catheter. The fluid injected by the powered fluid injector 100 can be, for example, a contrast fluid, a non-contrast fluid (e.g., saline), or a combination thereof. By injecting a quantity of fluid into a patient, the powered fluid injector 100 can facilitate a variety of medical diagnostic and/or interventional procedures, including the collection of image data representing an anatomical region of interest. These procedures can include, as examples, optical coherence tomography (OCT) imaging, intravascular ultrasound (IVUS) imaging, computed tomography (CT) imaging, magnetic resonance imaging (MRI), angiographic procedures, and interventional device procedures/placements.

The illustrated powered fluid injector 100 includes a drive assembly housing 102 (also referred to herein as an "injector housing") and a sleeve 104. The sleeve 104 can be secured to the drive assembly housing 102. For example, the drive assembly housing 102 can include an opening, and the sleeve 104 can be secured to the drive assembly housing 102 at or near such opening. The sleeve 104 may extend out from the drive assembly housing 102 and may be configured to receive and hold a reservoir 106 (also referred to herein as a "fluid reservoir"). The reservoir 106 can have an internal reservoir volume containing a fluid and can include a plunger 108 within the internal reservoir volume. Plunger 108 may be made of various components, including a wiper configured to be proximally and distally movable within the interior of fluid reservoir 106 and a ram extending from drive assembly housing 102 into sleeve 104 and being configured to engage the wiper when fluid reservoir 106 is received and secured in sleeve 104 and to drive the wiper proximally and distally in accordance with instructions received from controller 110 coupled to drive assembly housing 102. At least a portion of a drive assembly can be housed within the drive assembly housing 102.

The drive assembly can be configured to pressurize fluid within the internal reservoir volume. For instance, the drive assembly may couple to the plunger 108, such as at the opening in the drive assembly housing 102, and drive the plunger 108 within the internal reservoir volume. As the plunger 108 is progressively driven within the fluid reservoir 106, fluid within the internal reservoir volume can be output from the fluid reservoir 106 along tubing 109 leading to a catheter 126 that is inserted into a patient's blood vessel to inject the fluid into the vasculature. In certain applications of the powered fluid injector 100, output fluid, such as contrast media, can be pressurized anywhere from 1000-1500 psi (e.g., 1200 psi).

The illustrated example of the powered fluid injector 100 includes several features that can be useful in pressurizing and delivering fluid during operation. The powered fluid injector 100 can include a controller 110. The controller 110 can include a user interface for various operational aspects. For example, the controller 110 can be utilized by a user to set up various parameters and/or protocols to be used for a given fluid injection procedure. In one example, the user can interact with the controller 110 to input fluid injection parameters such as flow rate, injection volume (e.g., maximum), injection pressure limit (e.g., maximum), fluid injection duration, rise time, and/or other injection parameters. In one example, the controller 110 includes a touch-screen panel display, enabling a user to view and modify injection parameters. The controller 110 can also be used to initialize the powered fluid injector 100 (e.g., to prepare it for a patient fluid injection), or to activate certain features or sequences of operation. The controller 110 may also provide status information, including information related to past or currently ongoing injection procedures as well as any appropriate alerts. The controller 110 can include an imaging engine having one or more processors for controlling operation of the powered fluid injector 100. Such processors can also control other components, such as the drive assembly, a peristaltic pump 112, when present, and/or any sensors and detectors included at the powered fluid injector 100.

In addition to the controller 110, the illustrated powered fluid injector 100 includes a hand-control device 113 for user input. The hand-control device 113 can be coupled to the powered fluid injector 100 and the controller 110 either wirelessly or via a lined connection. As shown, the hand-control device 113 connects to drive assembly housing 102. In other examples, the hand-control device 113 can be connected directly to the controller 110. The hand-control device 113 can generate and send various signals related to an injection procedure to the controller 110 or other connected component. A user can actuate one or more interface components at the hand-control device 113 to control an injection procedure. For example, the user can use hand-control device 113 as a variable-rate control device to alter the fluid flow rate output from the powered fluid injector 100 and/or as a mechanism for starting or stopping a fluid injection. Hand-control device 113 may include an exterior body of the controller that is sized to be held in a single hand of a user. In other instances, hand-control device 113 may be sized differently, such as to be held in two hands of the user or to sit on a surface during operation.

The powered fluid injector 100 can also include one or more components useful for supplying fluid to be used in an injection procedure. A container 114 can include a supply of fluid, such as contrast media, and be secured to a holder 116 at the powered fluid injector 100. Fluid from the container 114 can be supplied to the fluid reservoir 106 for use during an injection procedure. For example, fluid from the container 114 can be drawn into the fluid reservoir 106 when the plunger 108 is being retracted and thereby refill the internal reservoir volume. Similarly, when the powered fluid injector 100 includes the peristaltic pump 112, a second container 118 can include a supply of fluid, such as a flushing medium (e.g., saline), and be secured to a holder 120 at the powered fluid injector 100. When present, the peristaltic pump 112 can receive fluid from the second container 118 and deliver such fluid to the patient. Often times, the peristaltic pump 112 may be used to deliver non-contrast fluid, such as saline, at a lower pressure than that at which the drive assembly delivers contrast fluid from the fluid reservoir 106. A valving system 124 can be included to selectively place the fluid reservoir 106 or peristaltic pump 112 in communication with the patient.

As described elsewhere herein, the controller 110 of the powered fluid injector 100 may control various functions of the powered fluid injector 100, which may include dispensing contrast fluid out through tubing. In some examples, the controller 110 may be housed in a housing of a display device. In some examples, the controller may be housed in the injector housing.

The powered fluid injector 100 may be connected to a catheter 126, fluidly and electrically, that is inserted into a blood vessel (e.g., the coronary artery) of a patient. When so connected, the powered fluid injector 100 can inject contrast fluid (of various concentrations) or dispense non-contrast fluid into the patient's vasculature via the injector tubing and the catheter 126. In many examples, the catheter 126 may include an invasive blood pressure sensor. The blood pressure sensor may be in electrical communication with the controller 110 when the powered fluid injector 100 is connected to the catheter 126. The blood pressure sensor may provide a blood pressure signal to the controller 110 when the catheter 126 is in fluidic connection with the powered fluid injector 100 and may not provide a blood pressure signal when the catheter 126 is not in fluidic connection with the powered fluid injector 100.

In accordance with the techniques described herein, hand-control device 113 may be modified to perform a variety of functions. For instance, hand-control device 113 may be configured to, in addition to sending signals to powered fluid injector 100, receive feedback from powered fluid injector 100, with the feedback providing an indication as to whether the command sent to powered fluid injector 100 was successful or unsuccessful, or even simply an indication representative of a status of powered fluid injector 100. For example, hand-control device 113 may include an input component at the controller body, with the input component being configured to receive user input. Hand-control device 113 may also include a communication unit. Responsive to the input component receiving the user input, the communication unit may be configured to generate an injection system command signal and convey the injection system command signal to powered fluid injector 100. Further, the communication unit may be configured to receive a controller command signal from powered fluid injector 100. Hand-control device 113 may also include an output component at the controller body, where the output component is configured to output an indication in response to the communication unit receiving the controller command signal from powered fluid injector 100.

In other instances, hand-control device 113 may be configured with multiple different input components, where one such input component controls the mode of operation for powered fluid injector 100 and where a second input component controls the action being performed in the particular mode of operation. For example, hand-control device 113 may include a first input component at the controller body, with the first input component being configured to receive user input identifying an injection system operational mode. In such examples, the communication unit may be configured to, in response to the first input component receiving the user input, generate an injection mode selection signal corresponding to the identified injection system operational mode and convey the injection mode selection signal to powered fluid injector 100. In addition to the first input component, hand-control device 113 may include a second input component at the controller body, with the second input component being configured to receive user input identifying an action command for the identified injection system operational mode. Responsive to the second input component receiving the user input, the communication unit may be further configured to generate an injection command signal corresponding to the identified action command and convey the injection command signal to the injection system.

In still other instances, hand-control device 113 may be configured to automatically start and stop refilling processes for various fluid reservoirs, including reservoir 106. Rather than basing this process on any direct input (e.g., pressing a button) on hand-control device 113, hand-control device 113 may detect movement or touching of hand-control device 113 and base the starting or stopping of the refilling process on the detected movement or touching (or lack thereof). For instance, the input component of hand-control device 113 may be configured to receive user input. Responsive to the input component receiving the user input, the communication unit may be configured to generate a first injection system command signal and convey the first injection system command signal to the injection system. Hand-control device 113 may further include a movement detection component at the controller body, with the movement detection component being configured to detect movement of the controller body. The communication unit may be further configured to, responsive to the movement detection component detecting movement of the controller body, generate a second injection system command signal and convey the second injection system command signal to the injection system.

Implementing hand-control device 113 into powered fluid injector 100 as described herein provides multiple benefits. For instance, rather than force the user to use a separate touchscreen (e.g., controller 110) to perform additional control functions, hand-control device 113 described herein may control additional functions without increasing the amount of input components present on hand-control device 113. Additionally, by providing feedback at hand-control device 113, a user of hand-control device 113 may maintain their focus on the patient and the activity being performed rather than divert their attention to a different system that the user must analyze to determine if the proper action was completed. Further, by automatically ceasing the refill operation of reservoir 106 in response to detecting movement of hand-control device 113, a user may decrease the amount of explicit inputs that must be entered on hand-control device 113, thereby increasing the efficiency of the refill operation, as well as the durability of hand-control device 113 itself. In the same vein, by automatically resuming the refill operation of reservoirs in response to detecting a lack of movement or contact, the various fluid reservoirs used by powered fluid injector 100 may refill at the most efficient and effective times, ensuring that the fluid is available when needed by the operator of powered fluid injector 100.

Additionally, and importantly, the operator of hand-control device 113 must be sterile. However, controller 110, which previously controlled these functions, is not sterile. As such, the operator, such as a cardiologist, must either instruct another individual, who may not be a trained cardiologist, as to what actions must be performed by powered fluid injector 100, or the cardiologist must themselves perform the functions on controller 110 and then re-sterilize themselves before operating hand-control device 113 again. By adding functionality to hand-control device 113, the amount of functionality that the operator may control personally and without having to touch an unsterile surface is greatly increased, thereby increasing the efficiency and efficacy of the overall powered fluid injector 100.

Figure 2A:
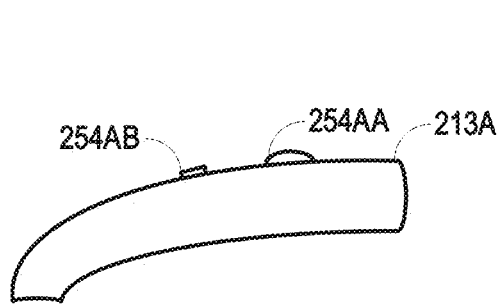
FIGS. 2A-2F are conceptual diagrams illustrating example hand-control devices with various configurations and that are each configured to perform one or more aspects of the techniques described in this disclosure.
Figure 2B:
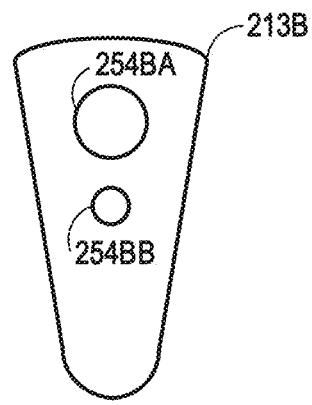
Figure 2C:
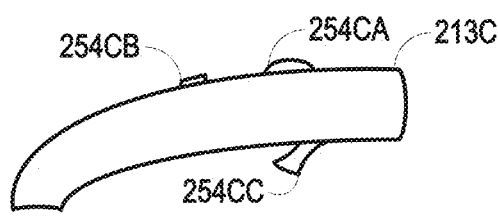
Figure 2D:
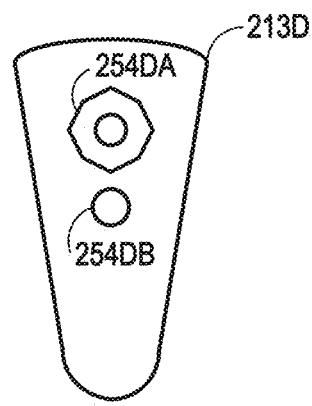
Figure 2E:
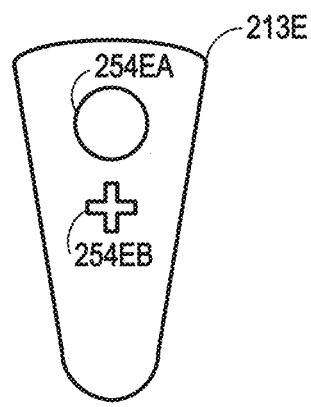
Figure 2F:
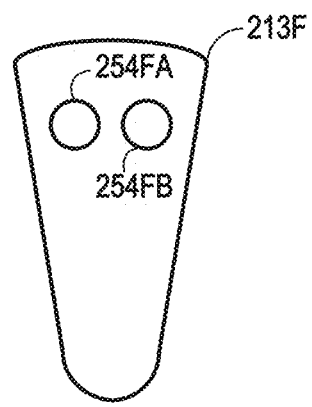
Figure 3:
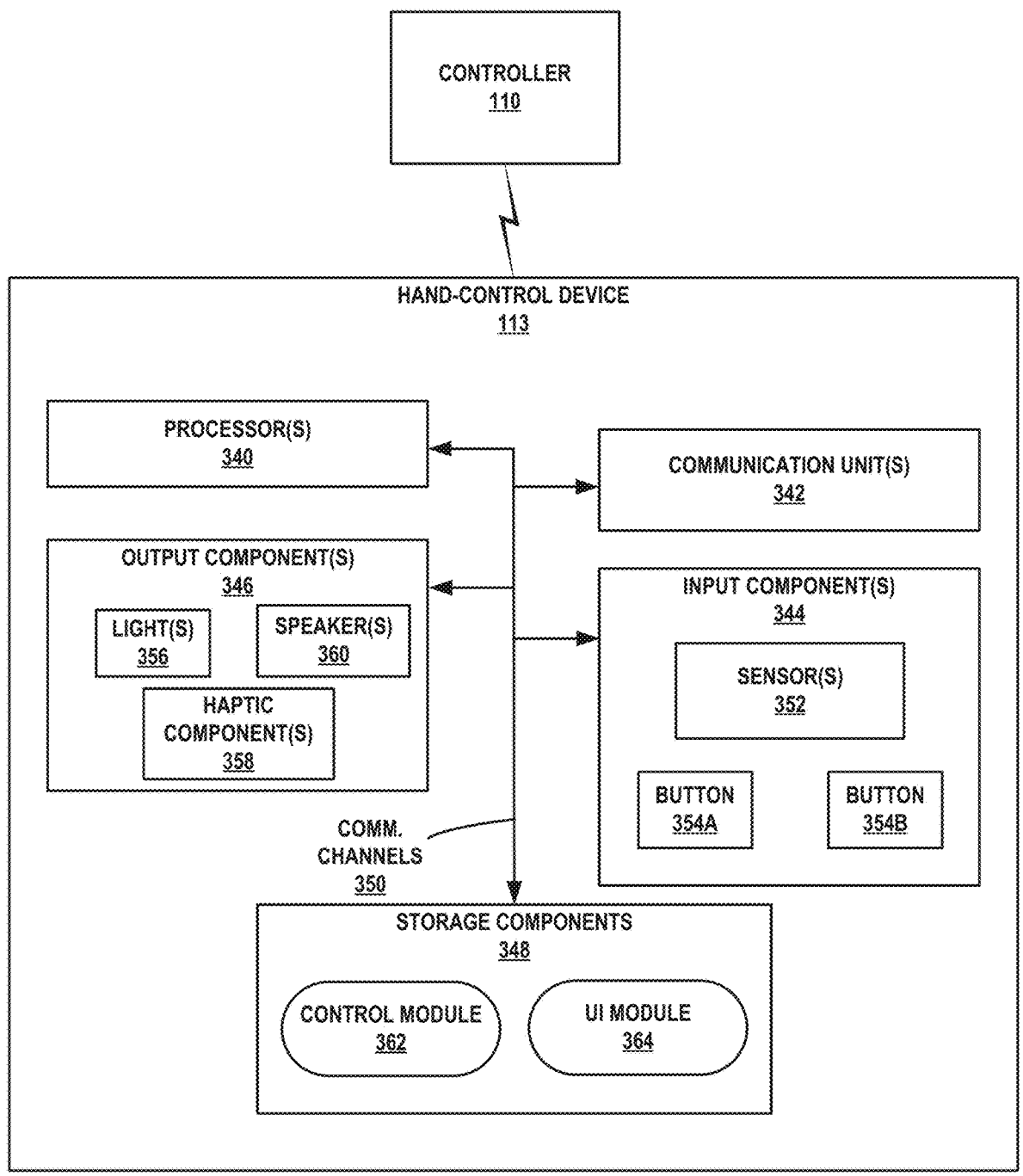
FIG. 3 is a block diagram illustrating an example hand-control device configured to control one or more aspects of an injection system, in accordance with one or more aspects of the techniques described in this disclosure.

FIGS. 2A-2F are conceptual diagrams illustrating example hand-control devices, with similar functional capabilities as hand-control device 113 of FIG. 1 and hand-control device 113 of FIG. 3, that may be configured to control one or more aspects of an injection system, in accordance with one or more aspects of the techniques described in this disclosure. Each example in FIGS. 2A-2F shows either a different view of an example configuration of a hand-control device or a different example of button configurations possible for hand-control devices as described herein. While various examples are shown in FIGS. 2A-2F, these examples should not be considered the only possible configurations of a hand-control device capable of performing the techniques described herein. Any combination of the shown devices or any other use of buttons or input components may be used in lieu of any example of FIGS. 2A-2F. For instance, rather than a mechanical button, the hand-control device may utilize a touch screen, a lever, or any other type of input component could be used.

FIG. 2A illustrates a side view of hand-control device 213A that may be configured to perform one or more aspects of the techniques described herein. In the example of FIG. 2A, hand-control device 213A includes button 254AA and button 254AB. Receiving input as a button press of button 254AA and/or button 254AB may initialize the performance of one or more aspects of the techniques described herein. For instance, receiving a press of one of button 254AA or button 254AB may cause hand-control device to generate an injection system command signal corresponding to the pressure and displacement of the button press. In other words, the particular injection system signal generated by hand-control device 213A may be dependent on the pressure applied to the particular one of buttons 254AA or 254AB or a distance that the particular one of buttons 254AA or 254AB is pressed from its neutral position. In other instances, a press received for button 254AA may cause hand-control device 213A to generate an injection mode selection signal corresponding to the pressure and displacement of the button press, while button 254AB may cause hand-control device 213A to generate an injection command signal corresponding to the pressure and displacement of the button press, or vice versa.

FIG. 2B illustrates a top view of hand-control device 213B that may be configured to perform one or more aspects of the techniques described herein. In the example of FIG. 2B, hand-control device 213B includes button 254BA and button 254BB. Receiving input as a button press of button 254BA and/or button 254BB may initialize the performance of one or more aspects of the techniques described herein. For instance, receiving a press of one of button 254BA or button 254BB may cause hand-control device to generate an injection system command signal corresponding to the pressure and displacement of the button press. In other words, the particular injection system signal generated by hand-control device 213B may be dependent on the pressure applied to the particular one of buttons 254BA or 254BB or a distance that the particular one of buttons 254BA or 254BB is pressed from its neutral position. In other instances, a press received for button 254BA may cause hand-control device 213B to generate an injection mode selection signal corresponding to the pressure and displacement of the button press, while button 254BB may cause hand-control device 213B to generate an injection command signal corresponding to the pressure and displacement of the button press, or vice versa.

FIG. 2C illustrates a side view of hand-control device 213C that may be configured to perform one or more aspects of the techniques described herein. In the example of FIG. 2C, hand-control device 213C includes button 254CA, button 254CB, and trigger 254CC. Receiving input as a button press of button 254CA and/or button 254CB may initialize the performance of one or more aspects of the techniques described herein. For instance, receiving a press of one of button 254CA or button 254CB may cause hand-control device to generate an injection system command signal corresponding to the pressure and displacement of the button press. In other words, the particular injection system signal generated by hand-control device 213C may be dependent on the pressure applied to the particular one of buttons 254CA or 254CB or a distance that the particular one of buttons 254CA or 254CB is pressed from its neutral position. In other instances, a press received for button 254CA may cause hand-control device 213C to generate an injection mode selection signal corresponding to the pressure and displacement of the button press, while button 254CB may cause hand-control device 213C to generate an injection command signal corresponding to the pressure and displacement of the button press, or vice versa. Further, trigger 254CC may further alter the signals generated by hand-control device 254C. For instance, an amount of pressure applied to trigger 254CC or a distance the trigger is pulled may initiate a 50/50 mix of fluid used during the injection or may adjust the percentages of the components in the solution used in the injection process.

FIG. 2D illustrates a top view of hand-control device 213D that may be configured to perform one or more aspects of the techniques described herein. In the example of FIG. 2A, hand-control device 213D includes joystick 254DA and button 254DB. Receiving input as a directed force applied to joystick 254DA or a button press of button 254DB may initialize the performance of one or more aspects of the techniques described herein. For instance, receiving a directed force applied to joystick 254DA or a button press of button 254DB may cause hand-control device to generate an injection system command signal corresponding to the direction or pressure of the directed force or the pressure and displacement of the button press. In other words, the particular injection system signal generated by hand-control device 213D may be dependent on the direction the user moves joystick 254DA, the amount of pressure applied to joystick 254DA, the pressure applied to button 254AB, or a distance that button 254DB is pressed from its neutral position. In other instances, a direction or pressure of the directed force received for joystick 254DA may cause hand-control device 213D to generate an injection mode selection signal corresponding to the pressure and/or direction of the directed force, while button 254DB may cause hand-control device 213D to generate an injection command signal corresponding to the pressure and displacement of the button press, or vice versa.

FIG. 2E illustrates a top view of hand-control device 213E that may be configured to perform one or more aspects of the techniques described herein. In the example of FIG. 2E, hand-control device 213E includes button 254EA and directional pad 254EB. Receiving input as a button press of one of button 254EA and/or a direction of directional pad 254EB may initialize the performance of one or more aspects of the techniques described herein. For instance, receiving a press of one of button 254EA or a direction of directional pad 254EB may cause hand-control device to generate an injection system command signal corresponding to the pressure and displacement of the button press, as well as the particular direction of directional pad 254EB that was pressed. In other words, the particular injection system signal generated by hand-control device 213E may be dependent on the pressure applied to the particular one of button 254EA or a particular direction of directional pad 254EB, a distance that the particular one of button 254EA or directional pad 254EB is pressed from its neutral position, or which particular direction of directional pad 254EB is pressed. In other instances, a press received for button 254EA may cause hand-control device 213E to generate an injection mode selection signal corresponding to the pressure and displacement of the button press, while directional pad 254EB may cause hand-control device 213E to generate an injection command signal corresponding to the pressure, displacement, and direction of the button press, or vice versa.

FIG. 2F illustrates a top view of hand-control device 213F that may be configured to perform one or more aspects of the techniques described herein. In the example of FIG. 2F, hand-control device 213F includes button 254FA and button 254FB, similar to hand-control device 213A of FIG. 2A, but with buttons 254FA and 254FB being laterally arranged rather than longitudinally arranged. Receiving input as a button press of one of buttons 254FA and/or button 254FB may initialize the performance of one or more aspects of the techniques described herein. For instance, receiving a press of button 254FA or button 254FB may cause hand-control device to generate an injection system command signal corresponding to the pressure and displacement of the button press. In other words, the particular injection system signal generated by hand-control device 213F may be dependent on the pressure applied to the particular one of buttons 254FA or 254FB or a distance that the particular one of buttons 254FA or 254FB is pressed from its neutral position. In other instances, a press received for button 254FA may cause hand-control device 213F to generate an injection mode selection signal corresponding to the pressure and displacement of the button press, while button 254FB may cause hand-control device 213F to generate an injection command signal corresponding to the pressure and displacement of the button press, or vice versa.

FIG. 3 is a block diagram illustrating an example hand-control device 113 configured to control one or more aspects of an injection system, in accordance with one or more aspects of the techniques described in this disclosure. Hand-control device 113 of FIG. 3 is described below as an example of hand-control devices 113 of FIG. 1 and FIGS. 2A-2F. FIG. 3 illustrates only one particular example of hand-control device 113, and many other examples of hand-control device 113 may be used in other instances and may include a subset of the components included in example hand-control device 113 or may include additional components not shown in FIG. 3.

As shown in the example of FIG. 3, hand-control device 113 includes one or more processors 340, one or more communication units 342, one or more input components 344, one or more output components 346, and one or more storage components 348. Input components include one or more sensors 352, button 354A, and button 354B. Output components 346 may include one or more lights 356, one or more haptic components 358, and one or more speakers 360. Storage components 348 of hand-control device 113 include control module 362 and UI module 364.

One or more processors 340 may implement functionality and/or execute instructions associated with hand-control device 113. That is, processors 340 may implement functionality and/or execute instructions associated with hand-control device 113 to communicate with controller 110 to control one or more aspects of an injection system.

Examples of processors 340 include application processors, display controllers, auxiliary processors, one or more sensor hubs, and any other hardware configure to function as a processor, a processing unit, or a processing device. Modules 362 and 364 may be operable by processors 340 to perform various actions, operations, or functions of hand-control device 113. For example, processors 340 of hand-control device 113 may retrieve and execute instructions stored by storage components 348 that cause processors 340 to perform the operations described with respect to modules 362 and 364. The instructions, when executed by processors 340, may cause hand-control device 113 to generate and output one or more command signals the control one or more aspects of an injection system.

One or more storage components 348 within hand-control device 113 may store information for processing during operation of hand-control device 113 (e.g., hand-control device 113 may store data accessed by modules 362 and 364 during execution at hand-control device 113). In some examples, storage component 348 is a temporary memory, meaning that a primary purpose of storage component 348 is not long-term storage. Storage components 348 on hand-control device 113 may be configured for short-term storage of information as volatile memory and therefore not retain stored contents if powered off. Examples of volatile memories include random access memories (RAM), dynamic random access memories (DRAM), static random access memories (SRAM), and other forms of volatile memories known in the art.

Storage components 348, in some examples, also include one or more computer-readable storage media. Storage components 348 in some examples include one or more non-transitory computer-readable storage mediums. Storage components 348 may be configured to store larger amounts of information than typically stored by volatile memory. Storage components 348 may further be configured for long-term storage of information as non-volatile memory space and retain information after power on/off cycles. Examples of non-volatile memories include magnetic hard discs, optical discs, floppy discs, flash memories, or forms of electrically programmable memories (EPROM) or electrically erasable and programmable (EEPROM) memories. Storage components 348 may store program instructions and/or information (e.g., data) associated with modules 362 and 364. Storage components 348 may include a memory configured to store data or other information associated with modules 362 and 364.

Communication channels 350 may interconnect each of the components 340, 342, 344, 346, and 348 for inter-component communications (physically, communicatively, and/or operatively). In some examples, communication channels 350 may include a system bus, a network connection, an inter-process communication data structure, or any other method for communicating data.

One or more communication units 342 of hand-control device 113 may communicate with external devices (e.g., controller 110) via one or more wired and/or wireless networks by transmitting and/or receiving network signals on one or more networks. Examples of communication units 342 include a network interface card (e.g. such as an Ethernet card), an optical transceiver, a radio frequency transceiver, a GPS receiver, or any other type of device that can send and/or receive information. Other examples of communication units 342 may include short wave radios, cellular data radios, wireless network radios, as well as universal serial bus (USB) controllers.

One or more input components 344 of hand-control device 113 may receive input. Examples of input are tactile, audio, and video input. Input components 344 of hand-control device 113, in one example, includes a presence-sensitive input device (e.g., a touch sensitive screen, a PSD), mouse, keyboard, voice responsive system, camera, microphone or any other type of device for detecting input from a human or machine. In some examples, input components 344 may include one or more sensor components 352—for example, one or more location sensors (GPS components, Wi-Fi components, cellular components), one or more temperature sensors, one or more movement sensors (e.g., accelerometers, gyros), one or more pressure sensors (e.g., barometer), one or more ambient light sensors, and one or more other sensors (e.g., infrared proximity sensor, hygrometer sensor, and the like).

Input components 344 may also include buttons 354A-354B (collectively buttons 354). In some instances, buttons 354 may be mechanical in nature, where the physical movement of buttons 354 activate the initiation of a function associated with the respective button. For instance, buttons 354 may be pressable, sinking into the body of hand-control device 113 when pressed. In other instances, buttons 354 may be switches, wherein the movement of buttons 354 in a plane apart from hand-control device 113 activate the initiation of the function associated with buttons 354. In some examples, an amount of pressure applied to buttons 354 may affect the command performed by the injection system. For instance, as more pressure is applied to buttons 354, an extent of the action performed by buttons 354 may increase (e.g., as more pressure is applied to one of buttons 354, a rate at which fluid is injected into a patient may increase). In other instances, buttons 354 may be graphical in nature and output for display on a presence-sensitive display. In such instances, when hand-control device 113 receives indications of user input interacting with the graphical buttons 354, processors 340 may activate the initiation of a function associated with buttons 354.

When input components 344 include a presence-sensitive display, the presence-sensitive display may be a screen at which information (e.g., a visual indication) is displayed while also detecting an object at and/or near the presence-sensitive display. While illustrated as an internal component of hand-control device 113, input components 344 may also represent an external component that shares a data path with hand-control device 113 for transmitting and/or receiving input and output. For instance, in one example, input components 344 represent a built-in component of hand-control device 113 located within and physically connected to the external packaging of hand-control device 113 (e.g., a screen on hand-control device 113). In another example, input components 344 represents an external component of hand-control device 113 located outside and physically separated from the packaging or housing of hand-control device 113 (e.g., a monitor, a projector, etc. that shares a wired and/or wireless data path with hand-control device 113).

When input components 344 of hand-control device 113 include the presence-sensitive display, input components 344 may detect two-dimensional and/or three-dimensional gestures as input from a user of hand-control device 113. For instance, sensors 352 may detect a user's movement (e.g., moving a hand, an arm, a pen, a stylus, tactile object, etc.) within a threshold distance of the sensor of input components 344. Input components 344 may determine a two or three-dimensional vector representation of the movement and correlate the vector representation to a gesture input (e.g., a hand-wave, a pinch, a clap, a pen stroke, etc.) that has multiple dimensions. In other words, input components 344 can detect a multi-dimension gesture without requiring the user to gesture at or near a screen or surface at which input components 344 outputs information for display. Instead, input components 344 can detect a multi-dimensional gesture performed at or near a sensor which may or may not be located near the screen or surface at which input components 344 outputs information for display.

One or more output components 346 of hand-control device 113 may generate output in a selected modality. Examples of modalities may include a tactile notification (output via one or more haptic components 358), audible notification (output via one or more speakers 360), visual notification (output via one or more lights 356), machine generated voice notification (output via one or more speakers 360), or other modalities. Output components 346 of hand-control device 113, in one example, includes a presence-sensitive display, sound card, video graphics adapter card, speaker, cathode ray tube (CRT) monitor, liquid crystal display (LCD), or any other type of device for generating output to a human or machine in a selected modality.

In general, control module 362 may be operable by processors 340 to control communication unit 342 in performing various communication functions with the injection system. Further, user interface (UI) module 364 may be operable by processors 340 to control input components 344 and output components 346 in receiving various inputs and outputting various indications. As such, in the disclosure, a function attributed to communication unit 342 is performed by processors 340 executing control module 362 to cause communication unit 342 to perform the function. Similarly, any input received by input components 344 may be equivalent to UI module 364 receiving an indication of user input via input components 344, and processors 340 may execute UI module 364 to control output components 346 in outputting various indications.

In accordance with the techniques described herein, hand-control device 113 may be modified to perform a variety of functions. For instance, hand-control device 113 may be configured to, in addition to sending signals to an injection system (e.g., powered fluid injector 100 of FIG. 1), receive feedback from the injection system, with the feedback providing an indication as to whether the command sent to the injection system was successful or unsuccessful, or even simply an indication representative of a status of the injection system. For example, hand-control device 113 may include input components 344 at the controller body (e.g., button 354A), with input components 344 being configured to receive user input.

Hand-control device 113 may also include communication unit 342. Responsive to input components 344 receiving the user input, communication unit 342 may be configured to generate an injection system command signal and convey the injection system command signal to the injection system. In some instances, the injection system command signal corresponds to an operational aspect of the injection system. For example, when button 354A or button 354B receives an indication of user input, communication unit 342 may generate the injection system command signal that may represent a command for the injection system to change from a first injection mode to a second, different injection mode. Examples of these various injection modes include a contrast fluid injection, a flushing fluid injection, a contrast and saline mixture fluid injection, a puff fluid injection, a pre-injection purge, and a sub-mode of any one of the contrast fluid injection, the flushing fluid injection, the contrast and saline mixture fluid injection, the puff fluid injection, or the pre-injection purge. For instance, in any of the injection modes, a sub-mode could change the location of the injection, such as from a right coronary injection to a left coronary injection.

In other instances, the indication of user input received at button 354A or button 354B may be a result of the user wishing to command the injection system to perform some function. As such, communication unit 342 may generate the injection system command signal to represent a command for the injection system. Examples of possible commands that communication unit 342 can convey to the injection system include starting a fluid injection, stopping a fluid injection, adjusting a fluid flow rate of a fluid injection, adjusting a duration of a fluid injection, adjusting a ratio of a contrast and saline mixture, starting a refill, stopping a refill, putting the injector into "standby" mode, and arming the injector.

Further, communication unit 342 may be configured to receive a controller command signal from the injection system. In general, the controller command signal is a communication to hand-control device 113 from the injection system regarding any characteristic of the injection system. In some examples, the controller command signal corresponds to an operational aspect of the injection system. Examples of these operational aspects can include an injection of a contrast fluid, an injection of a flushing fluid, a pressure in a fluid delivery component, and a completion of an injection system setup. In some instances, the controller command signal corresponds to an operational mode of the injection system. In some examples a user may set hand-control device 113 down during a medical procedure and lose track of the location of hand-control device 113. In such examples, a user may provide input to controller 110 to find hand-control device 113, and controller 110 may send a controller command signal to hand-control device 113. In response, hand-control device 113 may provide output through one or more of output components 346 described below (e.g., beep, flash a light, vibrate, etc.) to aid the user in locating hand-control device 113. In other instances, the controller command signal can correspond to a warning that a parameter at the injection system differs from a predetermined threshold for the parameter, or an expiration of a predetermined time period since generating the injection system command signal. In other words, the controller command signal can be representative of or indicative of any characteristic of the injection system.

Hand-control device 113 may also include output components 346 at the controller body. Output components 346 may be configured to output an indication in response to communication unit 342 receiving the controller command signal from the injection system. In other words, output components 346 may output some sort of indication that is representative of the feedback received from the injection system and that conveys the feedback to the user of hand-control device 113 such that the user is informed as to the current status of the injection system. In some instances, the indication represents a confirmation that the operational aspect has been implemented at the injection system. For example, when the injection system command is to switch from a first injection mode to a second, different injection mode, the indication may represent confirmation that the injection system has changed from the first injection mode to the second, different injection mode. In other instances, the indication can be indicative of an operational aspect of the injection system, such as a rate at which fluid is being injected by the injection system or that some action is currently being performed by the injection system.

In some instances, the feedback may also be indicative of an alert. For instance, any of output components 346 may generate output indicative of a misplaced catheter, a notification that an injection would dissect a vessel, that a dispensed fluid limit has been reached or is close to being reached, or any other alert that would notify a user of hand-control device 113 that a corrective action or a different action may be needed.

In some instances, output components 346 include at least one light emitting component (e.g., light 356). In such instances, the indication may be an adjustment to light emission at light 356 in response to communication unit 342 receiving the controller command signal. In some instances, the controller command signal may correspond to the particular adjustment to the light emission at the at least one light emitting component. For instance, the light emission can have a particular pattern, brightness, color, or flash pattern that is indicative of a particular message representative of the feedback being conveyed from the injection system to hand-control device 113.

In other instances, output components 346 include at least one sound emitting component (e.g., speakers 360). In some such instances, the controller command signal may correspond to the particular sound that speakers 360 output. For instance, the particular audio output by speakers 360 can correspond to a particular message representative of the feedback being conveyed from the injection system to hand-control device 113.

In still other instances, output components 346 include a haptic feedback component (e.g., haptic components 358). In some such instances, the indication can include an adjustment to a degree of haptic feedback at haptic component 358 in response to the communication unit receiving the controller command signal. In other words, haptic component 358 may cause hand-control device 113 to vibrate in a particular manner (e.g., varying levels of intensity and varying patterns) or may provide varying levels of resistance to buttons 354A and 354B. The particular manner in which haptic component 358 causes hand-control device 113 to vibrate or the particular level of resistance provided to buttons 354A and 354B can be indicative of the feedback intended to be conveyed by the injection system to hand-control device 113.

In one example of output components 346 including haptic components 358, the controller command signal may correspond to an implementation of a change in injection mode at the injection system. As such, the adjustment to the degree of haptic feedback may include a change in vibration at haptic components 358. In another example, the controller command signal may correspond to a degree of pressure in a fluid delivery component. As such, the adjustment to the degree of haptic feedback may include a change in a tactile resistance at haptic components 358, and the change in tactile resistance at the haptic components 358 may correspond to the degree of pressure in the fluid delivery component.

Input components 344 and output components 346 may be separate components at hand-control device 113. In this way, input components 344 may be spaced along the controller body away from output components 346.

In some instances, input components 344 may further include sensors 352. Sensors 352 may be configured to determine one or more of a current orientation of hand-control device 113 or that a shift has occurred to the orientation of the hand-control device. In receiving the user input, sensors 352 detect one of the current orientation of hand-control device 113 or the shift in the orientation of hand-control device 113. Based at least in part on the detected current orientation of hand-control device 113 or the detected shift in the orientation of hand-control device 113, control module 362 may generate the particular command signal.

In other instances, hand-control device 113 may be configured with multiple different input components 344, where one such input component (e.g., button 354A) controls the mode of operation for the injection system and where a second input component (e.g., button 354B) controls the action being performed in the particular mode of operation. For example, hand-control device 113 may include a first input component (button 354A) at the controller body, with button 354A being configured to receive user input identifying an injection system operational mode. In such examples, communication unit 342 may be configured to, in response to button 354A receiving the user input, generate an injection mode selection signal corresponding to the identified injection system operational mode and convey the injection mode selection signal to the injection system. Examples of the injection system operational mode include a contrast fluid injection, a flushing fluid injection, a contrast and saline mixture fluid injection, a puff fluid injection, and a pre-injection purge.

In addition to button 354A, hand-control device 113 may include a second input component (button 354B) at the controller body. Button 354B may be configured to receive user input identifying an action command for the identified injection system operational mode. In some instances, button 354A and button 354B are separate components at the hand-control device such that button 354A is spaced along the controller body from button 354B. Button 354A and button 354B may have additional differences. For instance, button 354A may be shaped like a first geometric shape and button 354B may be shaped like a second, different geometric shape. In other instances, button 354A may be located at a first surface of the controller body and button 354B may be located at a second surface of the controller body. The first surface may spaced from the second surface approximately ninety degrees relative to a center point of the controller body (e.g., button 354A may be located on a top surface of hand-control device 113 and button 354B may be located on a front surface of hand-control device 113). In other instances, the first surface may be spaced from the second surface approximately one hundred and eighty degrees relative to a center point of the controller body (e.g., button 354A may be located on a top surface of hand-control device 113 and button 354B may be located on a bottom surface of hand-control device 113).

In some examples, button 354A and/or button 354B may be configured to receive user input by movement of the respective input component and within a range of different angular positions relative to a surface of the controller body at which the at least one of button 354A and button 354B is located. For example, button 354A and/or button 354B may be a lever or a joystick-type structure, there a user may push and pull the lever/joystick to activate and deactivate the respective button.

Responsive to button 354B receiving the user input, communication unit 342 may be further configured to generate an injection command signal corresponding to the identified action command and convey the injection command signal to the injection system. For example, the action command may include a starting an action under the identified injection system operational mode or a stopping of an action under the identified injection system operational mode.

In some instances, communication unit 342 may only generate and/or convey the injection command signal if an injection mode is selected. For example, communication unit 342 may, in some instances, generate the injection command signal corresponding to the identified action command and convey the injection command signal to the injection system in response to the user input at button 354B only if button 354A has received user input.

In still other instances, hand-control device 113 may be configured to automatically start and stop refilling processes for various fluid reservoirs, such as reservoir 106 of FIG. 1. Rather than basing this process on any direct input (e.g., pressing a button) on hand-control device 113, sensors 352 of hand-control device 113 may detect movement or touching of hand-control device 113 and base the starting or stopping of the refilling process on the detected movement or touching (or lack thereof). For instance, input components 344 of hand-control device 113 may be configured to receive user input. Responsive to input components 344 receiving the user input, communication unit 342 may be configured to generate a first injection system command signal and convey the first injection system command signal to the injection system. In some instances, the first injection system command signal may represent a command for the injection system to start an injection of contrast fluid from a contrast fluid reservoir (e.g., reservoir 106 of FIG. 1).

Hand-control device 113, may further include a movement detection component (e.g., sensors 352) at the controller body, with sensors 352 being configured to detect movement of the controller body. For instance, sensors 352 may include an accelerometer having a first acceleration detection axis and a second, different acceleration detection axis.

Communication unit 342 may be further configured to, responsive to sensors 352 detecting movement of the controller body, generate a second injection system command signal and convey the second injection system command signal to the injection system. For instance, when sensors 352 include the accelerometer, communication unit 342 may be configured to generate the second injection system command signal in response to sensors 352 detecting acceleration along one of the first acceleration detection axis and the second, different acceleration detection axis exceeding a preset acceleration threshold.

In order to instruct communication unit 342 to generate the second injection system command signal, sensors 352 may be configured to provide an indication of input to communication unit 342 in response to the movement detection component detecting movement of the controller body. In the instances when communication unit 342 is generating the second injection system command signal in response to sensors 352 detecting the movement of the controller body, the second injection system command signal may be a refill termination signal. As such, communication unit 342 may generate the refill termination signal and convey the refill termination signal to the injection system in response to sensors 352 detecting the movement of the controller body. The refill termination signal may represent a command for the injection system to terminate a contrast refill operation at a contrast fluid reservoir of the injection system, where the contrast refill operation includes introducing contrast fluid into the contrast fluid reservoir. Terminating refill of the contrast fluid reservoir upon detection of movement of the controller body may enable an operator to begin an injection operation as soon as he/she picks up the hand-control device.

In addition to detecting instances of movement for hand-control device 113, sensors 352 may also detect when no movement of hand-control device 113 has occurred for a predetermined time period. Responsive to sensors 352 detecting no movement of the controller body for the predetermined time period, communication unit 342 may be configured to generate a refill initiation signal and convey the refill initiation signal to the injection system. The refill initiation signal may represent a command for the injection system to initiate a contrast refill operation at a contrast fluid reservoir of the injection system, and wherein the contrast refill operation comprises introducing contrast fluid into the contrast fluid reservoir. Automatically refilling the contrast fluid reservoir may ensure that refill occurs when the operator is not holding the hand-control device, thereby making effective use of otherwise idle time. In some examples, the automatic refill operation and the automatic refill termination operation can ensure that the injection system is filling the contrast fluid reservoir while the hand-control device is sitting idle but cease such filling as soon as the hand-control device is picked up.

In some examples, output components 346 may be configured to output an indication in response to the movement detection component detecting no movement of the controller body for the predetermined time period, thereby indicating that the contrast refill operation is in progress. The indication can be one or more of a light emission (output by lights 356), a sound emission (output by speakers 360), and haptic feedback (output by haptic components 358).

Implementing hand-control device 113 into powered fluid injector 100 as described herein provides multiple benefits. For instance, rather than force the user to use a separate touchscreen (e.g., controller 110) to perform additional control functions, hand-control device 113 described herein may control additional functions without increasing the amount of input components present on hand-control device 113. Additionally, by providing feedback at hand-control device 113, a user of hand-control device 113 may maintain their focus on the patient and the activity being performed rather than divert their attention to a different system that the user must analyze to determine if the proper action was completed. Further, by automatically ceasing the refill operation of reservoir 106 in response to detecting movement of hand-control device 113, a user may decrease the amount of explicit inputs that must be entered on hand-control device 113, thereby increasing the efficiency of the refill operation, as well as the durability of hand-control device 113 itself. In the same vein, by automatically resuming the refill operation of reservoirs in response to detecting a lack of movement or contact, the various fluid reservoirs used by powered fluid injector 100 may refill at the most efficient and effective times, ensuring that the fluid is available when needed by the operator of powered fluid injector 100.

Additionally, and importantly, the operator of hand-control device 113 must be sterile in most instances. However, controller 110, which previously controlled these functions, is not sterile. As such, the operator, such as a cardiologist, must either instruct another individual, who may not be a trained cardiologist, as to what actions must be performed by powered fluid injector 100, or the cardiologist must themselves perform the functions on controller 110 through a sterile drape, which may limit functionality. By adding functionality to hand-control device 113, the amount of functionality that the operator may control personally and without having to deal with a sterile drape is greatly increased, thereby increasing the efficiency and efficacy of the overall powered fluid injector 100.

Figure 4:
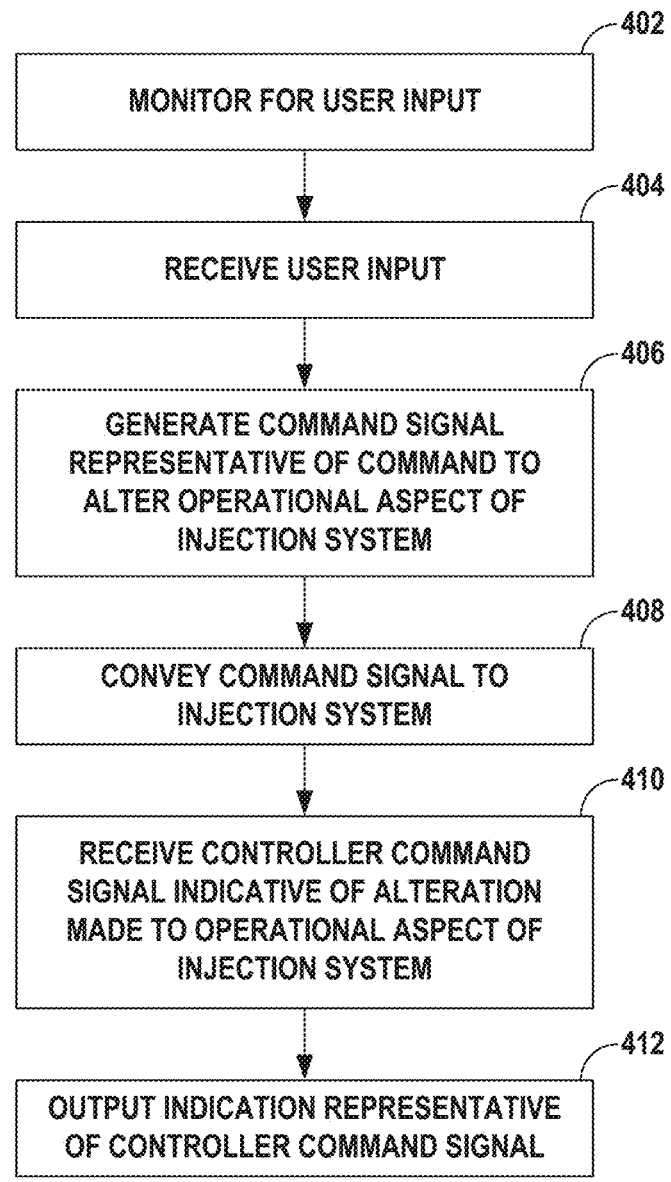
FIG. 4 is a flowchart illustrating an example process for a hand-control device to facilitate two-way communication with an injection system, in accordance with one or more aspects of the techniques described in this disclosure.

FIG. 4 is a flowchart illustrating an example process for a hand-control device to facilitate two-way communication with an injection system, in accordance with one or more aspects of the techniques described in this disclosure. The techniques of FIG. 4 may be performed by one or more processors of a computing device, such as hand-control device 113 of FIGS. 1-3. For purposes of illustration only, the techniques of FIG. 4 are described within the context of hand-control device 113 of FIG. 3, although computing devices having configurations different than that of hand-control device 113 may perform the techniques of FIG. 4.

In accordance with the techniques described herein, UI module 364 monitors hand-control device 113 for any indications of user input (402). UI module 364 then receives such user input via input components 344 (404). Control module 362 generates, via communication units 342, a command signal representative of a command to alter some operational aspect of the injection system (406). Control module 362 conveys, via communication units 342, the command signal to the injection system (408). Control module 362 receives, via communication units 342, a controller command signal indicative of an alteration made to some operational aspect of the injection system, such as a success message, a warning message, or some other feedback (410). Control module 362 outputs an indication representative of the controller command signal (412).

Figure 5:
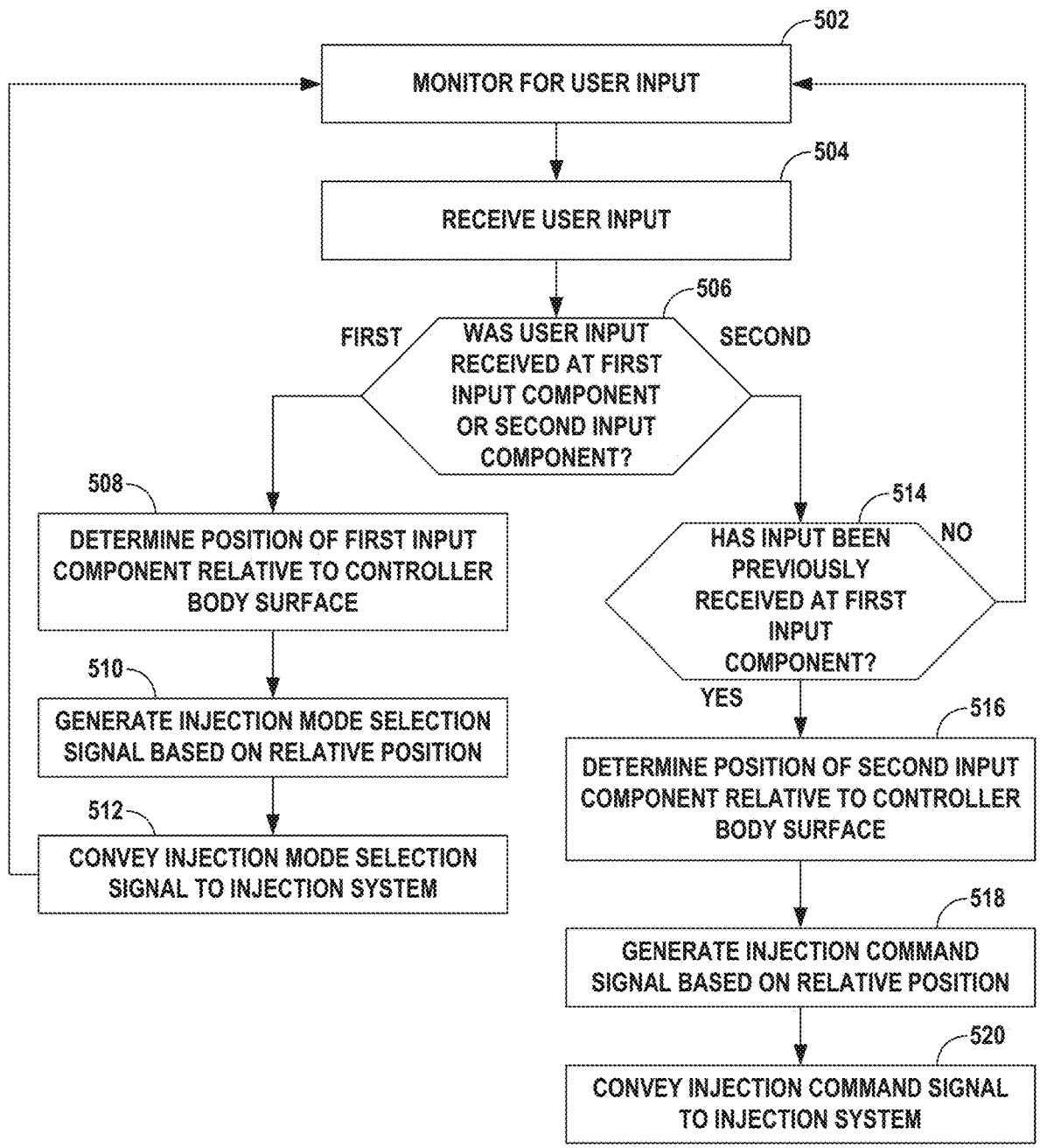
FIG. 5 is a flowchart illustrating an example process for a hand-control device to control an injection system with different mode and action input components, in accordance with one or more aspects of the techniques described in this disclosure.

FIG. 5 is a flowchart illustrating an example process for a hand-control device to control an injection system with different mode and action input components, in accordance with one or more aspects of the techniques described in this disclosure. The techniques of FIG. 5 may be performed by one or more processors of a computing device, such as hand-control device 113 of FIGS. 1-3. For purposes of illustration only, the techniques of FIG. 5 are described within the context of hand-control device 113 of FIG. 3, although computing devices having configurations different than that of hand-control device 113 may perform the techniques of FIG. 5.

In accordance with the techniques described herein, UI module 364 monitors hand-control device 113 for any indications of user input (502). UI module 364 then receives such user input via input components 344 (504). UI module 364 determines whether the user input was received at button 354A or button 354B (506).

If UI module 364 determines that the user input was received at button 354A ("FIRST" branch of 506), UI module 364 determines a position of button 354A relative to a controller body surface of hand-control device 113 (e.g., an angular position or a percentage that button 354A is depressed) (508). Control module 362 generates an injection mode selection signal based on the determined relative position of button 354A (510) and conveys, via communication units 342, the injection mode selection signal to the injection system (512).

Conversely, if UI module 364 determines that the user input was received at button 354B ("SECOND" branch of 506), UI module 364 determines whether input was previously received at button 354A to select the injection mode (514). If UI module 364 has not received any indications of user input at button 354A ("NO" branch of 514), UI module 364 continues to monitor for user input (502). If UI module 364 determines that button 354A has received user input and a mode is selected ("YES" branch of 514), UI module 364 determines a position of button 354B relative to a controller body surface of hand-control device 113 (e.g., an angular position or a percentage that button 354B is depressed) (516). Control module 362 generates an injection command signal based on the determined relative position of button 354B (518) and conveys, via communication units 342, the injection command signal to the injection system (520).

Figure 6:
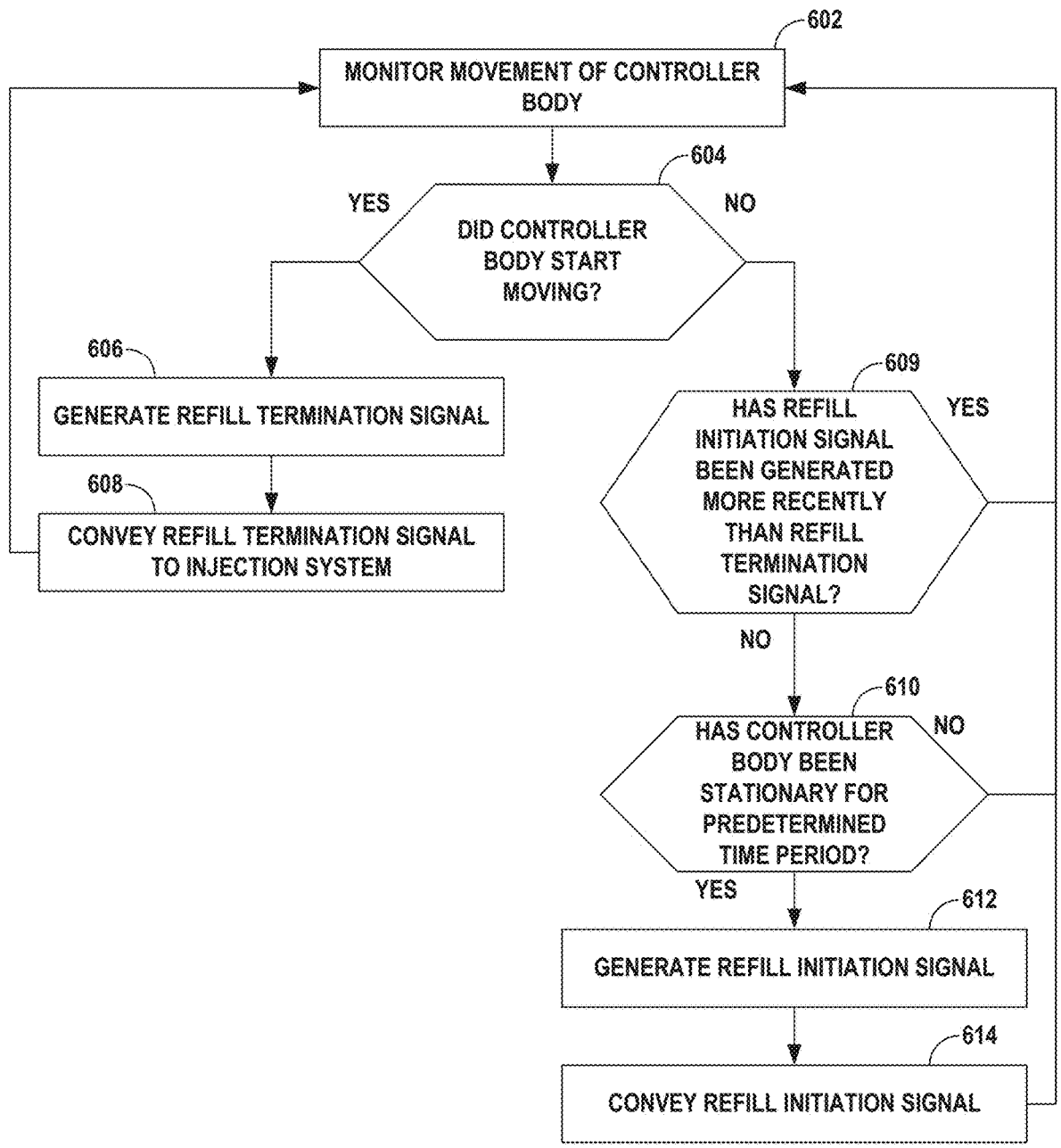
FIG. 6 is a flow chart illustrating an example process for a hand-control device to facilitate the automatic starting and stopping of a refill procedure for an injection system, in accordance with one or more aspects of the techniques described in this disclosure.

FIG. 6 is a flow chart illustrating an example process for a hand-control device to facilitate the automatic starting and stopping of a refill procedure for an injection system, in accordance with one or more aspects of the techniques described in this disclosure. The techniques of FIG. 6 may be performed by one or more processors of a computing device, such as hand-control device 113 of FIGS. 1-3. For purposes of illustration only, the techniques of FIG. 6 are described within the context of hand-control device 113 of FIG. 3, although computing devices having configurations different than that of hand-control device 113 may perform the techniques of FIG. 6.

In accordance with the techniques described herein, UI module 364 monitors, using sensors 352, hand-control device 113 for any movement of the controller body (602). UI module 364, at any point, determines whether the controller body started moving (604). If UI module 364 determines that the controller body did start moving ("YES" branch of 604), control module 362 generates a refill termination signal (606). Control module 362 then conveys, via communication units 342, the refill termination signal to the injection system (608).

Conversely, if UI module 364 determines that the controller body is not moving ("NO" branch of 604), control module 362 determines whether a refill initiation signal has been generated more recently than a refill termination signal (609). In this way, control module 362 determines whether the injection system is currently performing a refill operation. In other words, if a refill initiation signal was generated more recently than a refill termination signal, control module 362 may determine that the injection system is already in the refilling process or that the refill process has been completed before the controller body has moved. In either case, generating an additional refill initiation signal may be superfluous. As such, if the refill initiation signal has been generated more recently than a refill termination signal ("YES" branch of 609), UI module 364 continues to monitor the controller body for movement (602). In some instances, control module 362 itself may be the entity that produced the last signal sent to the injection system. In other instances, controller 110, such as a touchscreen controller, may have generated the signal. Control module 362 may be configured to check both hand-control device 113 and controller 110 in determining whether the refill initiation signal or the refill termination signal was generated more recently.

If, on the other hand, control module 362 determines that a refill termination signal was generated more recently than a refill initiation signal ("NO" branch of 609), UI module 364 determines whether the controller body has been stationary for a predetermined time period (610). If the controller body has not been stationary for the predetermined time period ("NO" branch of 610), UI module 364 continues to monitor the controller body for movement (602). Conversely, if UI module 364 determines that the controller body has been stationary for the predetermined time period ("YES" branch of 610), control module 362 generates a refill initiation signal (612). Control module 362 then conveys, via communication units 342, the refill initiation signal to the injection system (614).

While described as starting or terminating a refill operation based on whether the controller body is moving or remaining stationary, sensors 352 in the controller body can be used for other functions. For instance, control module 362 may generate a command signal that is based on an orientation of the controller body, as determined by sensors 352. For instance, control module 362 may generate a refill initiation signal upon sensors 352 determining that the controller body is substantially vertical (e.g., within 5 to 10 degrees of vertical), or upon determining that the controller body has shifted from a substantially horizontal (e.g., within 5 to 10 degrees of horizontal) position to a substantially vertical position. Similarly, control module 362 may generate a refill termination signal upon sensors 352 determining that the controller body is substantially horizontal (e.g., within 5 to 10 degrees of horizontal), or upon determining that the controller body has shifted from a substantially vertical (e.g., within 5 to 10 degrees of vertical) position to a substantially horizontal position. While the examples described above describe the specific example of refill initiation and termination signals based on the orientation of the controller body, in other instances, any command described herein, or any command suitable for this type of controller, can be generated by any particular orientation of the controller body, or by any particular shift from one orientation of the controller body to another different orientation.

Figure 7:
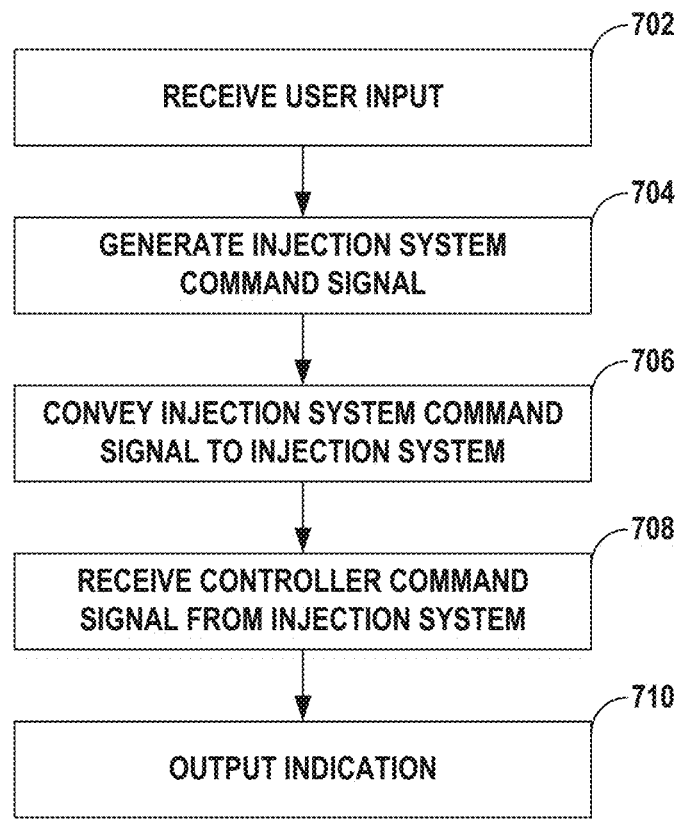
FIG. 7 is a flowchart illustrating an example process for a hand-control device to facilitate two-way communication with an injection system, in accordance with one or more aspects of the techniques described in this disclosure.

FIG. 7 is a flowchart illustrating an example process for a hand-control device to facilitate two-way communication with an injection system, in accordance with one or more aspects of the techniques described in this disclosure. The techniques of FIG. 7 may be performed by one or more processors of a computing device, such as hand-control device 113 of FIGS. 1-3. For purposes of illustration only, the techniques of FIG. 7 are described within the context of hand-control device 113 of FIG. 1, although computing devices having configurations different than that of hand-control device 113 may perform the techniques of FIG. 7.

In accordance with the techniques described herein, hand-control device 113 may receive user input at an input component (702). Responsive to the input component receiving the user input, hand-control device 113 generates an injection system command signal (704) and conveys the injection system command signal to powered fluid injector 100 (706). Further, hand-control device 113 receives a controller command signal from powered fluid injector 100 (708). Hand-control device 113 outputs an indication in response to the communication unit receiving the controller command signal from powered fluid injector 100 (710).

Figure 8:
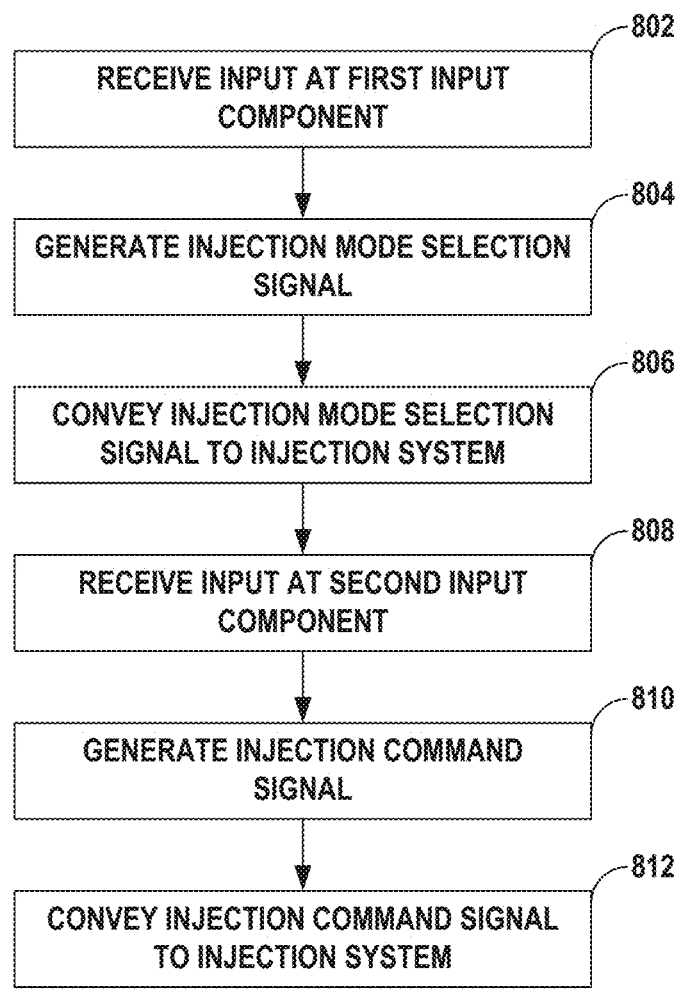
FIG. 8 is a flowchart illustrating an example process for a hand-control device to control an injection system with different mode and action input components, in accordance with one or more aspects of the techniques described in this disclosure.

FIG. 8 is a flowchart illustrating an example process for a hand-control device to control an injection system with different mode and action input components, in accordance with one or more aspects of the techniques described in this disclosure. The techniques of FIG. 8 may be performed by one or more processors of a computing device, such as hand-control device 113 of FIGS. 1-3. For purposes of illustration only, the techniques of FIG. 8 are described within the context of hand-control device 113 of FIG. 1, although computing devices having configurations different than that of hand-control device 113 may perform the techniques of FIG. 8.

In accordance with one or more techniques of this disclosure, hand-control device 113 may receive user input identifying an injection system operational mode at a first input component (802). Responsive to the first input component receiving the user input, hand-control device 113 generates an injection mode selection signal corresponding to the identified injection system operational mode (804) and conveys the injection mode selection signal to powered fluid injector 100 (806). Hand-control device 113 may receive, at a second input component at the controller body, user input identifying an action command for the identified injection system operational mode (808). Responsive to the second input component receiving the user input, hand-control device 113 generates an injection command signal corresponding to the identified action command (810) and conveys the injection command signal to the injection system (812).

Figure 9:
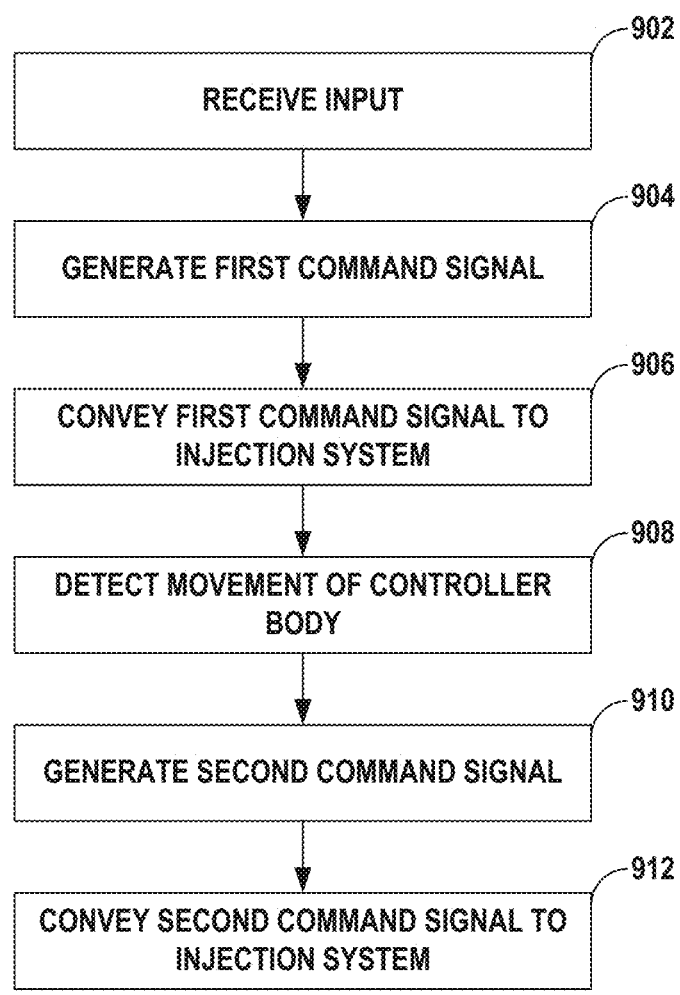
FIG. 9 is a flow chart illustrating an example process for a hand-control device to facilitate the automatic starting and stopping of a refill procedure for an injection system, in accordance with one or more aspects of the techniques described in this disclosure.

FIG. 9 is a flow chart illustrating an example process for a hand-control device to facilitate the automatic starting and stopping of a refill procedure for an injection system, in accordance with one or more aspects of the techniques described in this disclosure. The techniques of FIG. 9 may be performed by one or more processors of a computing device, such as hand-control device 113 of FIGS. 1-3. For purposes of illustration only, the techniques of FIG. 9 are described within the context of hand-control device 113 of FIG. 1, although computing devices having configurations different than that of hand-control device 113 may perform the techniques of FIG. 9.

In accordance with one or more techniques of this disclosure, hand-control device 113 receives user input at an input component (902). Responsive to the input component receiving the user input, hand-control device 113 generates a first injection system command signal (904) and conveys the first injection system command signal to the injection system (906). Hand-control device 113 detects movement of the controller body with a movement detection component (908). Responsive to the movement detection component detecting movement of the controller body, hand-control device 113 generates a second injection system command signal (910) and conveys the second injection system command signal to the injection system (912).

Figure 10:
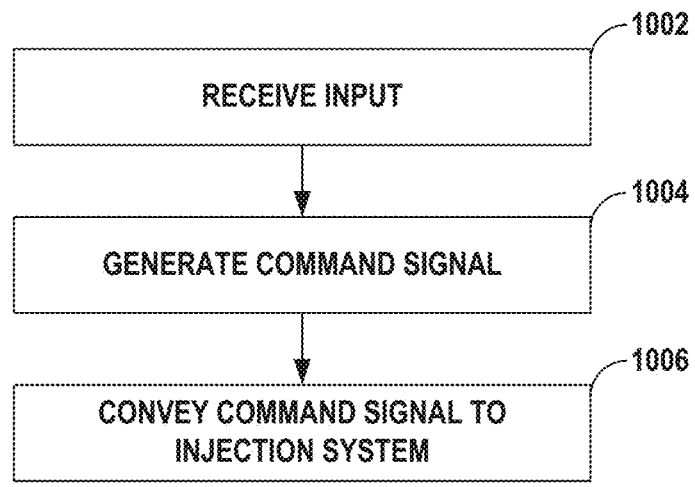
FIG. 10 is a flow chart illustrating an example process for a hand-control device to communicate with an injection system, in accordance with one or more aspects of the techniques described in this disclosure.

FIG. 10 is a flow chart illustrating an example process for a hand-control device to communicate with an injection system, in accordance with one or more aspects of the techniques described in this disclosure. The techniques of FIG. 10 may be performed by one or more processors of a computing device, such as hand-control device 113 of FIGS. 1-3. For purposes of illustration only, the techniques of FIG. 10 are described within the context of hand-control device 113 of FIG. 1, although computing devices having configurations different than that of hand-control device 113 may perform the techniques of FIG. 10.

In accordance with one or more techniques of this disclosure, hand-control device 113 may receive user input (1002). Responsive to receiving the user input, hand-control device 113 generates a command signal (1004). Hand-control device conveys the command signal to an injection system (1006).

It is to be recognized that depending on the example, certain acts or events of any of the techniques described herein can be performed in a different sequence, may be added, merged, or left out altogether (e.g., not all described acts or events are necessary for the practice of the techniques). Moreover, in certain examples, acts or events may be performed concurrently, e.g., through multi-threaded processing, interrupt processing, or multiple processors, rather than sequentially.

In one or more examples, the functions described may be implemented in hardware, software, firmware, or any combination thereof. If implemented in software, the functions may be stored on or transmitted over as one or more instructions or code on a computer-readable medium and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media which is non-transitory or (2) a communication medium such as a signal or carrier wave. Data storage media may be any available media that can be accessed by one or more computers or one or more processors to retrieve instructions, code and/or data structures for implementation of the techniques described in this disclosure. A computer program product may include a computer-readable medium.

By way of example, and not limitation, such computer-readable storage media can comprise RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transitory media, but are instead directed to non-transitory, tangible storage media. Disk and disc, as used herein, includes compact disc (CD), laser disc, optical disc, digital versatile disc (DVD), floppy disk and Blu-ray disc, where disks usually reproduce data magnetically, while discs reproduce data optically with lasers. Combinations of the above should also be included within the scope of computer-readable media.

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein. In addition, in some aspects, the functionality described herein may be provided within dedicated hardware and/or software modules configured for encoding and decoding, or incorporated in a combined codec. Also, the techniques can be fully implemented in one or more circuits or logic elements.

The techniques of this disclosure may be implemented in a wide variety of devices or apparatuses, including a wireless handset, an integrated circuit (IC) or a set of ICs (e.g., a chip set). Various components, modules, or units are described in this disclosure to emphasize functional aspects of devices configured to perform the disclosed techniques, but do not necessarily require realization by different hardware units. Rather, as described above, various units may be combined in a codec hardware unit or provided by a collection of interoperative hardware units, including one or more processors as described above, in conjunction with suitable software and/or firmware.

Various examples of the disclosure have been described. Any combination of the described systems, operations, or functions is contemplated. These and other examples are within the scope of the following claims.

What is claimed is:

1. A hand-control device for a powered fluid injection system, including a controller, the hand-control device comprising:
   a controller body sized to be held in a single hand of a user;
   an input component at the controller body, wherein the input component is configured to receive a user input, said input component including one or more sensors for detecting one of a current orientation of the hand-control device, a shift in an orientation of the hand-control device, a movement or a touching of the hand-control device;
   a communication unit configured to, responsive to the user input received by the input component:
      generate an injection system command signal based at least in part on said current orientation, shift in the orientation, movement or touching or lack of movement or lack of touching of the hand-control device;
      convey the injection system command signal to the injection system; and
      receive a controller command signal from the injection system; and
   an output component at the controller body, wherein the output component is configured to output an indication in response to the controller command signal received by the communication unit and generated by the injection system.

2. The hand-control device of claim 1, wherein the injection system command signal corresponds to an operational aspect of the injection system, and wherein the indication represents a confirmation that the operational aspect has been implemented at the injection system.

3. The hand-control device of claim 2, wherein the injection system command signal represents a command for the injection system to change from a first injection mode to a second, different injection mode, and wherein the indication represents confirmation that the injection system has changed from the first injection mode to the second, different injection mode.

4. The hand-control device of claim 3, wherein at least one of the first injection mode comprises one or more of a contrast fluid injection, a flushing fluid injection, a contrast and saline mixture fluid injection, a puff fluid injection, a pre-injection purge, or a sub-mode of any one of the contrast fluid injection, the flushing fluid injection, the contrast and saline mixture fluid injection, the puff fluid injection, or the pre-injection purge.

5. The hand-control device of claim 2, wherein the injection system command signal represents a command for the injection system, wherein the command comprises one or more of starting a fluid injection, stopping a fluid injection, adjusting a fluid flow rate of a fluid injection, adjusting a duration of a fluid injection, and adjusting a ratio of a contrast and saline mixture.

6. The hand-control device of claim 1, wherein the controller command signal corresponds to an operational aspect of the injection system, and wherein the indication represents the operational aspect.

7. The hand-control device of claim 6, wherein the operational aspect of the injection system comprises one or more of an injection of a contrast fluid, an injection of a flushing fluid, a pressure in a fluid delivery component, and a completion of an injection system setup.

8. The hand-control device of claim 1, wherein the output component includes at least one light emitting component, and wherein the indication comprises a particular adjustment to light emission at the at least one light emitting component in response to the controller command signal received by the communication unit.

9. The hand-control device of claim 8, wherein the controller command signal corresponds to the particular adjustment to the light emission at the at least one light emitting component be adjusted.

10. The hand-control device of claim 1, wherein the output component includes at least one sound emitting component, and wherein the controller command signal corresponds to a particular sound output by the at least one sound emitting component.

11. The hand-control device of claim 1, wherein the output component includes a haptic feedback component, and wherein the indication comprises an adjustment to a degree of haptic feedback at the haptic feedback component in response to the communication unit receiving the controller command signal.

12. The hand-control device of claim 11, wherein the controller command signal corresponds to implementation of a change in injection mode at the injection system, and wherein the adjustment to the degree of haptic feedback comprises a change in vibration at the haptic feedback component.

13. The hand-control device of claim 11, wherein the controller command signal corresponds to a degree of pressure in a fluid delivery component, wherein the adjustment to the degree of haptic feedback comprises a change in a tactile resistance at the haptic feedback component, and wherein the change in tactile resistance at the haptic feedback component corresponds to the degree of pressure in the fluid delivery component.

14. The hand-control device of claim 1, wherein the input component and the output component are separate components at the hand-control device such that the input component is spaced along the controller body from the output component.

15. The hand-control device of claim 1, wherein the controller command signal corresponds to a warning that a parameter at the injection system differs from a predetermined threshold for the parameter.

16. The hand-control device of claim 1, wherein the controller command signal corresponds to an expiration of a predetermined time period since generating the injection system command signal.

17. The hand-control device of claim 1, wherein the input component comprises one or more sensors, wherein the user input received by the input component comprises the one or more sensors detecting one of a current orientation of the hand-control device or a shift in an orientation of the hand-control device, and wherein the injection system command signal is based at least in part on the current orientation of the hand-control device or the shift in the orientation of the hand-control device.

18. A hand-control device for a powered fluid injection system, including a controller the hand-control device comprising:
a controller body sized to be held in a single hand of a user;
a first input component at the controller body, wherein the first input component is configured to receive a first user input that identifies an injection system operational mode;
a communication unit configured to, responsive to the first user input received by the first input component:
generate an injection mode selection signal corresponding to the injection system operational mode; and
convey the injection mode selection signal to the injection system; and
a second input component at the controller body, wherein the second input component is configured to receive a second user input that identifies an action command for the injection system operational mode, said second input component including one or more sensors for detecting one of a current orientation of the hand-control device, a shift in an orientation of the hand-control device, a movement or a touching of the hand-control device,
wherein the communication unit is further configured to, responsive to the second user input received by the second input component:
generate an injection command signal corresponding to the action command, wherein the injection command signal is based at least in part on said current orientation, shift in the orientation, movement or touching or lack of movement or lack of touching of the hand-control device; and
convey the injection command signal to the injection system.

19. The hand-control device of claim 18, wherein the injection system operational mode comprises one of a contrast fluid injection, a flushing fluid injection, a contrast and saline mixture fluid injection, a puff fluid injection, and a pre-injection purge.

20. The hand-control device of claim 18, wherein the action command comprises one of a starting of the identified injection system operational mode and a stopping of the identified injection system operational mode.

21. The hand-control device of claim 18, wherein the communication unit is further configured to:
generate the injection command signal corresponding to the identified action command; and
convey the injection command signal to the injection system in response to the user input at the second input component only after the first input component has received user input.

22. The hand-control device of claim 18, wherein the first input component and the second input component are separate components at the hand-control device such that the first input component is spaced along the controller body from the second input component.

23. The hand-control device of claim 22, wherein the first input component comprises a first geometric shape and the second input component comprises a second, different geometric shape.

24. The hand-control device of claim 22, wherein the first input component is located at a first surface of the controller body and the second input component is located at a second surface of the controller body.

25. The hand-control device of claim 24, wherein the first surface is spaced from the second surface approximately ninety degrees relative to a center point of the controller body.

26. The hand-control device of claim 24, wherein the first surface is spaced from the second surface approximately one hundred and eighty degrees relative to a center point of the controller body.

27. The hand-control device of claim 18, wherein at least one of the first input component and the second input component is configured to receive user input by movement of the at least one of the first input component and the second input component within a range of different angular positions relative to a surface of the controller body at which the at least one of the first input component and the second input component is located.

28. A hand-control device for a powered fluid injection system, the hand-control device comprising:
a controller body sized to be held in a single hand of a user;
an input component at the controller body, wherein the input component is configured to receive user input;
a communication unit configured to, responsive to the user input received by the input component:
generate a first injection system command signal; and
convey the first injection system command signal to the injection system; and
a movement detection component at the controller body, wherein the movement detection component is configured to detect movement of the controller body,
wherein the communication unit is further configured to, responsive to detection of movement of the controller body by the movement detection component:
generate a second injection system command signal; and
convey the second injection system command signal to the injection system.

29. The hand-control device of claim 28, wherein the movement detection component is configured to provide an indication of input in response to detection of movement of the controller body by the movement detection component.

30. The hand-control device of claim 28, wherein the second injection system command signal comprises a refill termination signal, and wherein, responsive to detection of movement of the controller body by the movement detection component, the communication unit is configured to:
  generate the refill termination signal; and
  convey the refill termination signal to the injection system.

31. The hand-control device of claim 30, wherein the refill termination signal represents a command for the injection system to terminate a contrast refill operation at a contrast fluid reservoir of the injection system, and wherein the contrast refill operation comprises the introduction of contrast fluid into the contrast fluid reservoir.

32. The hand-control device of claim 31, wherein the first injection system command signal represents a command for the injection system to start an injection of contrast fluid from the contrast fluid reservoir.

33. The hand-control device of claim 28, wherein the movement detection component is configured to provide a second input in response to lack of detection of movement of the controller body by the movement detection component for a predetermined time period.

34. The hand-control device of claim 33, wherein, responsive to the lack of detection of movement of the controller body by the movement detection component for the predetermined time period, the communication unit is configured to:
  generate a refill initiation signal; and
  convey the refill initiation signal to the injection system.

35. The hand-control device of claim 34, wherein the refill initiation signal represents a command for the injection system to initiate a contrast refill operation at a contrast fluid reservoir of the injection system, and wherein the contrast refill operation comprises the introduction of contrast fluid into the contrast fluid reservoir.

36. The hand-control device of claim 28, further comprising:
  an output component at the controller body, wherein the output component is configured to output an indication in response to lack of detection of movement of the controller body by the movement detection component for a predetermined time period.

37. The hand-control device of claim 36, wherein the indication comprises one or more of a light emission, a sound emission, and haptic feedback.

38. The hand-control device of claim 28, wherein the movement detection component comprises an accelerometer having a first acceleration detection axis and a second, different acceleration detection axis, and wherein the communication unit is configured to:
  generate the second injection system command signal in response to acceleration along one of the first acceleration detection axis and the second, different acceleration detection axis exceeding a preset acceleration threshold.

* * * * *